United States Patent [19]

van der Jagt

[11] Patent Number: Plant 6,038

[45] Date of Patent: Oct. 13, 1987

[54] CHRYSANTHEMUM PLANT NAMED REKEL

[75] Inventor: Martinus van der Jagt, Ter Aar, Netherlands

[73] Assignee: Chrysanthemum Breeders Association, N.V., Curacao, Netherlands Antilles

[21] Appl. No.: 599,700

[22] Filed: Apr. 12, 1984

[30] Foreign Application Priority Data

May 10, 1983 [NL] Netherlands ..... CHR777

[51] Int. Cl.[4] ..... A01H 5/00

[52] U.S. Cl. ..... Plt./81

[58] Field of Search ..... Plt./81, 82

*Primary Examiner*—Robert E. Bagwill

*Attorney, Agent, or Firm*—Parkhurst & Oliff

[57] ABSTRACT

A new and distinct cultivar of Chrysanthemum plant named 'Rekel', bearing medium sized bronze-red blooms with a bronze-red center and having a performance of eighteen days.

3 Drawing Figures

BACKGROUND OF THE NEW PLANT

The new plant of the present invention relates to the Chrysanthemum genus.

ORIGIN AND HISTORY OF THE PLANT

The new plant according to the present invention comprises a new and distinct cultivar of Chrysanthemum plant which is a color mutant of Chrysanthemum named 'Reef'. The new cultivar was discovered by Martinus van der Jagt in May, 1982 at Paradijsweg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a medium sized bloom and bronze-red color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the fully mature bloom of the new cultivar;

Figure 1:
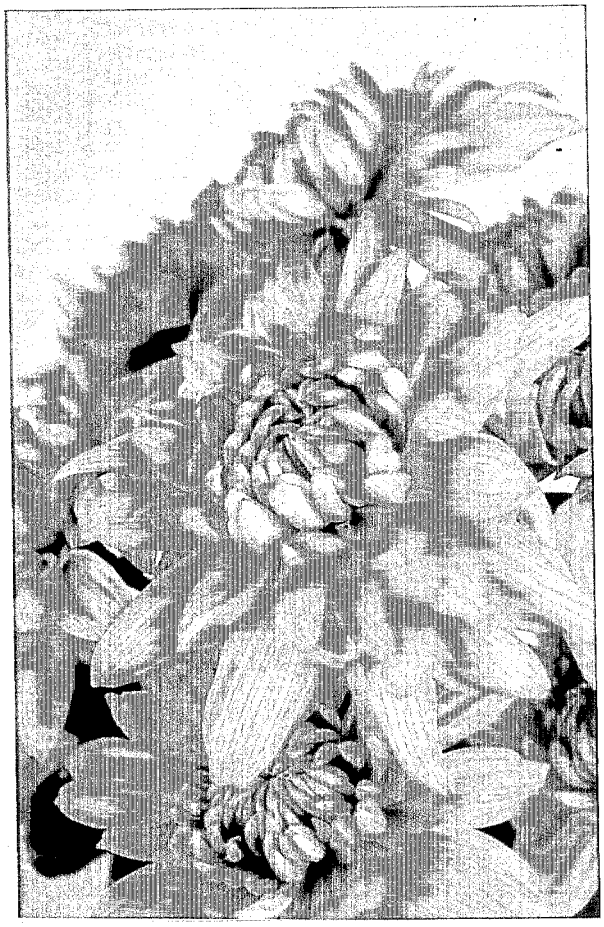
Figure 2:
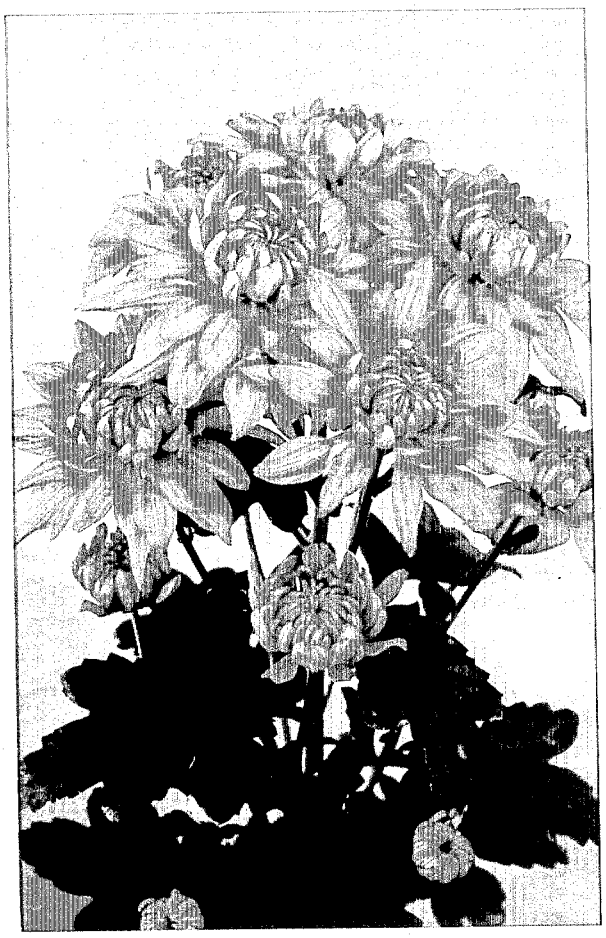
Figure 3:
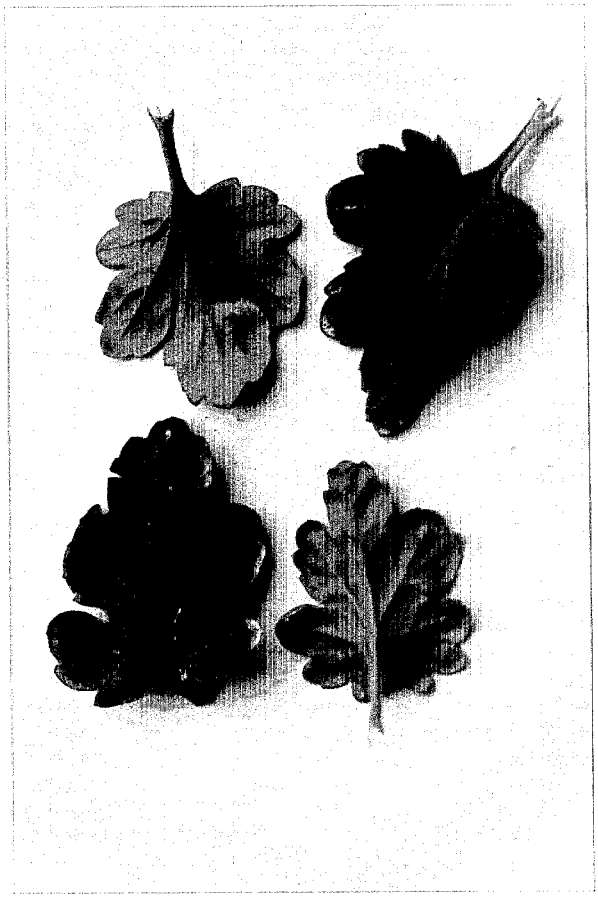

Sheet 2 shows various stages of bloom of the new cultivar; and

Sheet 3 shows the foliage and petiole of the new cultivar.

DESCRIPTION OF THE NEW PLANT

This new variety of Chrysanthemum is of the botanical classification *Chrysanthemum morifolium,* named "Rekel". When grown in the vicinity of Ter Aar, Holland, it has a response time of approximately nine and one-half weeks. This new variety produces medium sized bronze-red blooms with a bronze-red center having a performance of eighteen days. This new variety of Chrysanthemum has been found to retain its distinctive characteristics throughout successive propagations and may be planted under conventional greenhouse conditions in Holland.

The following is a description of the plant and characteristics that distinguish it over related known varieties and its antecedents:

Botanical classification: *Chrysanthemum morifolium.*

Bud:
- *Size.*—Large, cross section 1.7 cm., height 1.3 cm.
- *Form.*—Round and flat.
- *Outside color.*—Red RHS 46 A.

Bloom:
- *Size.*—Medium.
- *Fully expanded.*—7 cm.
- *Borne.*—Single.
- *Stems.*—Strong.
- *Forms.*—Decorative.
- *Permanence.*—18 days (at 18°-20° C.).

Color:
- *Center of flower (Disk Floret).*—Red RHS 46 A.
- *Base of petals.*—Red RHS 46 A.
- *Inside of petals.*—Red RHS 45 A.
- *Reverse of petals.*—Red RHS 45 A.
- *Outer petals.*—Red RHS 59 D.
- *Tonality from a distance.*—"Classical" decorative flower of a bronze-red color.
- *Fully matured (discoloration).*—Red RHS 59 D.

Petals:
- *Texture (upper and underside).*—Rough.
- *Number.*—In excess of 80.
- *Cross-section.*—Halfway tubular, convex at the end.
- *Arrangement.*—Imbricated.
- *Persistence.*—Normal. Outer petals reflex more when overbloomed.
- *Fragrance.*—Chrysanthemum.

Reproductive organs:
- *Stamen.*—A few in the tubular petals.
- *Pollen.*—None.
- *Styles.*—Columnar.
- *Length.*—Very short, 2 mm.
- *Stigmas.*—Very small, 0.5 mm. and smaller.
- *Ovaries.*—Enclosed in calyx (when present).

Plant:
- *Form.*—Single stem spray meant for erect culture.
- *Growth.*—Medium.
- *Height.*—95 cm.
- *Peduncle.*—Near the Top: 8 cm. Near the Middle: 14 cm. Near the Bottom: 15 cm.

*Internodes.*—2½–3 cm.

*Flowering response.*—Nine and one-half weeks.

Foliage:

*Color.*—Green.

*Size.*—Length 9 cm., width 7 cm.

*Quantity.*—30–38.

*Shape.*—Pointed and undulated.

*Texture.13* Upperside — Rough. Underside — Rough.

*Ribs and Veins.*—Both not so well developed. Upperside: Ribs and veins difficult to see. Underside: Ribs and veins clearly marked.

*Edge.*—Undulated.

*Leaf underside.*—Rough, minimum hirsuteness.

In the description above, color references are made to the "R.H.S Colour Chart" issued by The Royal Horticultural Society in association with the Flower Council of Holland, February 1986.

What is claimed is:

1. A new and distinct cultivar of Chrysanthemum named 'Rekel', as described and illustrated in the foregoing specification and accompanying drawings.

* * * * *